United States Patent [19]

Bischkopf et al.

[11] 4,177,544
[45] Dec. 11, 1979

[54] METHOD OF AND APPARATUS FOR MAKING TAMPONS

[75] Inventors: Gerd Bischkopf, Kottenheim; Herbert Gawarecki, Haltern-Flaesheim; Gerhard Cremer, Mayen, all of Fed. Rep. of Germany

[73] Assignee: Biloma GmbH Spezialmaschinenfabrik, Mayen, Fed. Rep. of Germany

[21] Appl. No.: 772,632

[22] Filed: Feb. 28, 1977

[30] Foreign Application Priority Data

Feb. 27, 1976 [DE] Fed. Rep. of Germany ....... 2607975

[51] Int. Cl.$^2$ ............................................. A61F 13/20
[52] U.S. Cl. ..................................................... 28/119
[58] Field of Search ............... 19/144.5, 149; 128/270, 128/285; 28/117, 118, 119

[56] References Cited

U.S. PATENT DOCUMENTS

| | | | |
|---|---|---|---|
| 2,094,086 | 9/1937 | Webb | 19/144.5 |
| 2,763,899 | 9/1956 | Niepmann et al. | 19/144.5 |
| 2,977,644 | 4/1961 | Wieser | 19/144.5 X |
| 4,019,226 | 4/1977 | Yamauchi et al. | 19/144.5 |

Primary Examiner—Dorsey Newton
Attorney, Agent, or Firm—Michael J. Striker

[57] ABSTRACT

A carousel rotatable about a fixed axis carries a plurality of treatment units which are mounted on the carousel removably for easy repair and replacement. A supply fixed adjacent the carousel feeds a strip of pressable material tangentially toward the carousel. Each of the units has a cutter for severing from this strip a portion of the pressable material, a gripper for holding the strip during such severing, a winder for rolling up each of the severed portions into a tampon blank, a press for compressing the tampon blank into a finished tampon, and a heater for heating and thermally fixing the finished tampon. These various devices are all controlled by at least one cam fixed adjacent the carousel and operatively engageable with the various elements of each unit for synchronously operating same and thereby automatically producing tampons at a high production rate.

23 Claims, 10 Drawing Figures

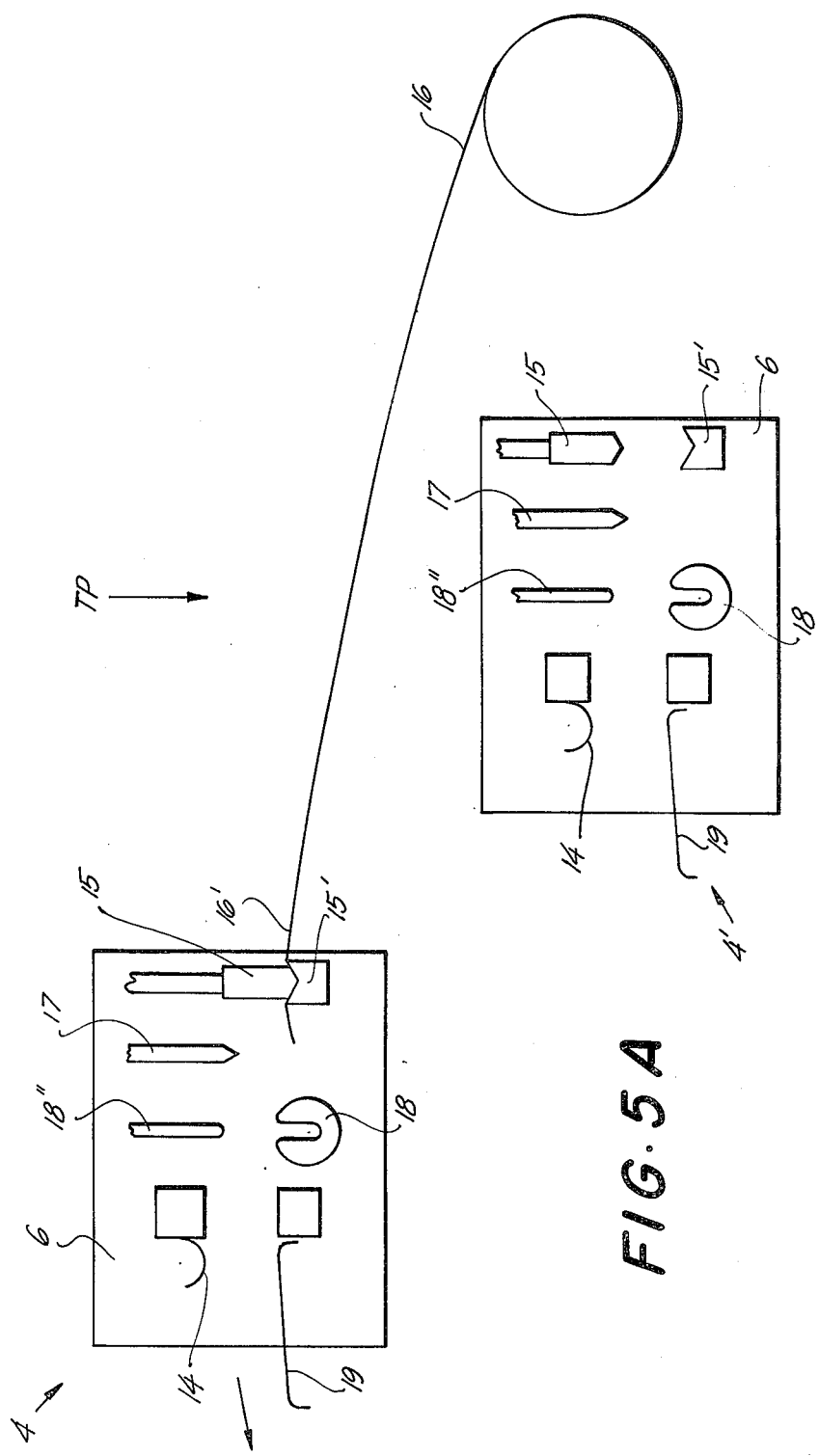

METHOD OF AND APPARATUS FOR MAKING TAMPONS

BACKGROUND OF THE INVENTION

The present invention relates to a method of and apparatus for making tampons. More particularly this invention concerns a fully automatic arrangement which produces feminine-hygiene tampons from a strip of pressable cotton-type material.

It is known to produce a feminine-hygiene tampon from a strip of cotton-like material by severing a portion from this strip, winding it up into a so-called tampon blank, pressing the blank to reduce its size and form it into a relatively unitary cylindrical body, and thereafter often heating the thus-pressed body to fix its shape and form a finished tampon which is then inserted into an applicator tube or the like. These four steps—severing, winding, pressing and heating—must be carried out often at separate locations. For this reason automatic mass production of such a product often is relatively complex and requires considerable machinery.

It has been suggested to combine the severing and winding operations in a single machine so as to produce the above-mentioned tampon blank. Such machinery is frequently very hard to control and operate, so that if anything goes wrong the entire machine and, therefore, the entire production operation must temporarily be shut down. In addition the transporting of the relatively fragile tampon blanks from this machine to the necessary pressing machine is problematic in that the blank frequently unwinds en route and therefore becomes unpressable.

Such a machine is frequently formed as a so-called carousel having a plurality of treatment units or stations which orbit past the supply of the strip material and carry out the necessary pressing operations. Although such a construction does aid in the automatic manufacture of small items such as tampons, it has the enormous disadvantage that whenever any one of the treatment units breaks down the entire carousel must be stopped. The same construction has been used also for the tampon press. Invariably the tampon press and the severing and winding units are separate, in order that they can be serviced separately and that disturbances to the one will not too greatly affect the other.

Various such machines can be seen in Swiss Pat. Nos. 334,460 and 393,631 as well as in U.S. Pat. No. 2,798,260 and British Pat. No. 630,104.

SUMMARY OF THE INVENTION

It is an object of the present invention to provide an improved machine for automatically making tampons.

Another object is to provide such a machine which automatically and continuously produces finished tampons from a strip of pressable material.

A further object of this invention is the provision of an improved method and apparatus for making tampons which allows any disturbances in the production to be relatively cured, and which operates in a simple and efficient manner at high speed.

These object are attained according to the present invention in an apparatus of the above-described general type having a carousel rotatable about a fixed carousel axis and carrying a plurality of treatment units which are secured releasably to the carousel at respective locations spaced angularly therearound for orbiting of these units about the carousel axis on rotation of the carousel. A supply is fixed adjacent the carousel axis for feeding a strip of pressable cotton-type material provided with spaced-apart retrieval chords to the carousel. Each of the units or stations on the carousel is provided with gripper means for holding the strip, cutting means for severing a portion from the strip, winding means for rolling up the portion into a tampon blank, and pressing means for compressing the tampon blank into a finished tampon. All of these various means at each of the units are operated by at least one cam fixed adjacent the carousel and operatively engaging all of the means for synchronously operating same.

In accordance with the present invention therefore the succession of angularly spaced treatment units or stations is orbited about the axis in a predetermined rotational sense so that each of the stations trails the station immediately downstream and leads the station immediately upstream. The end of the strip is gripped at a first one of the stations which, as it orbits, pulls the strip from the supply past a second one of the stations immediately trailing the first station. This second station grips the strip between its leading end and the supply and severs from the gripped strip at the second station a portion of the strip. This portion is then released from the first station and wound up at the second station into a tampon blank which is then pressed into a finished tampon and discharged from the second station. Meanwhile the steps of gripping the strip, severing the gripped strip, winding the severed portion, pressing the tampon blank, and discharging the finished tampon are sequentially repeated at a third station immediately trailing the second station, and thereafter at a fourth station immediately trailing the third station and so on.

In accordance with this invention the carousel is provided with at least eight, normally ten such units or stations and is rotated at a rate of at least five revolutions per minute, normally at least nine. Thus it is possible with this machine to produce ninety tampons per minute by producing one tampon in each station on each revolution thereof about the carousel axis.

Should any of the units malfunction or breakdown, it is a relatively simple matter to temporarily stop the carousel and disconnect the releasable mounting means, normally bolts, so as to remove the malfunctioning unit and replace it with a spare such unit which is in good working order. Thus downtime in the production line is minimized and the malfunctioning unit can readily be carried off to a shop for proper servicing.

According to yet another feature of this invention each unit is provided with a heating head rotatable on the respective unit about a respective head axis parallel to the carousel axis. This heating head is electrically resistively heated to a temperature of at least 100° C. and is formed with an annular array of angularly equispaced heating recesses. The pressing means of each unit has a pressing recess which can be decreased in size to the size the finished tampon should have. The heating recesses are axially alignable with this pressing recess, and the heating head is indexed so as to align a fresh empty hole with the pressing recess each time the carousel makes a full revolution. Thus, with twelve recesses in the head, the finished pressed tampons will be held in the heating head for at least 30 seconds, normally 45 seconds. Thereafter an ejector serves to push the finished tampons out of the heating head into applicator tubes or other packaging.

According to further features of this invention each of the units or stations is provided with an upstream gripper having a pair of holding elements capable of tightly clamping the strip upstream of the severing and winding units, and a downstream gripper having a pair of holding elements capable of holding the strip downstream of the winding and severing units with enough force to maintain tension in this strip, but still to allow it to be pulled between these downstream holding elements during winding-up of the strip portion. The winding unit itself is formed as a slotted mandrel tube between the severing blade of the severing unit and the downstream gripper. An inserting element serves to push the upstream end of the severed portion into the slot in the fork or mandrel, whereupon this pusher unit pulls out to leave the upstream end wedged in place in the mandrel and the mandrel turns to wind-up the severed strip.

The press itself according to this invention is of the general type described in U.S. Pat. No. 2,798,260 having a pair of centrally apertured plates flanking a plurality of segments capable of moving radially so as to increase and decrease the size of the pressing recess. This pressing recess is aligned axially between the mandrel and the above-mentioned pressing head. Once the tampon blank is wound up on the mandrel a support carrying the two grippers, the severing unit, and the winder is displaced axially toward the pressing arrangement so as to insert the tampon blank on the mandrel into the pressing recess. Thereafter a stripping element or plate on the above-mentioned support pushes the tampon blank off the mandrel as the entire support is withdrawn so as to leave this tampon blank in the press. The press is then closed to compress the tampon blank into the desired shape. Thereafter renewed advancing of the mandrel axially serves to push the now-pressed tampon blank through the pressing recess into one of the heating recesses.

According to yet another feature of this invention each unit is provided with means for rounding the end of the finished press tampon. This means comprises a concave element displaceable axially toward and away from the tampons held in the pressing head so as to round their ends. This is accomplished by bringing axially to bear on one end of tampons in the heating head a concave element while pushing the other end of the tampon with the pin that later serves to eject the tampon completely from the heating head.

In accordance with this invention each of the units or stations is almost entirely self-contained. All of the various functions except the closing of the pressing recess and the displacement of the rounding element are carried out by cooperation of cam followers with fixed cams adjacent the carousel. Simple compressed-air connections are made for operation of the press and the rounder, whose functions thereafter are controlled by cam-operated valves. In addition springs are provided on practically all of the various movable elements to hold them normally in desired positions. Thus the grippers are normally biased by springs into open positions out of engagement with the strip, the element serving to wedge the strip end into the mandrel is similarly spring biased out of engagement with the mandrel, and the severing blade is also spring biased out of the path of the strip.

Thus the system according to the present invention allows tampons to be produced at an extremely high production rate. A single machine forms the completed article. Any failure of any of the various units of this machine can readily be corrected by a simple replacement in a very short period of time of the malfunctioning unit. Thus the overall production rate can be held very high.

The novel features which are considered as characteristic for the invention are set forth in particular in the appended claims. The invention itself, however, both as to its construction and its method of operation, together with additional objects and advantages thereof, will be best understood from the following description of a specific embodiment when read in connection with the accompanying drawings.

BRIEF DESCRIPTION OF THE DRAWINGS:

FIGS. 5A–5F are largely schematic and partly sectional views illustrating operation of the apparatus.

Figure 1:
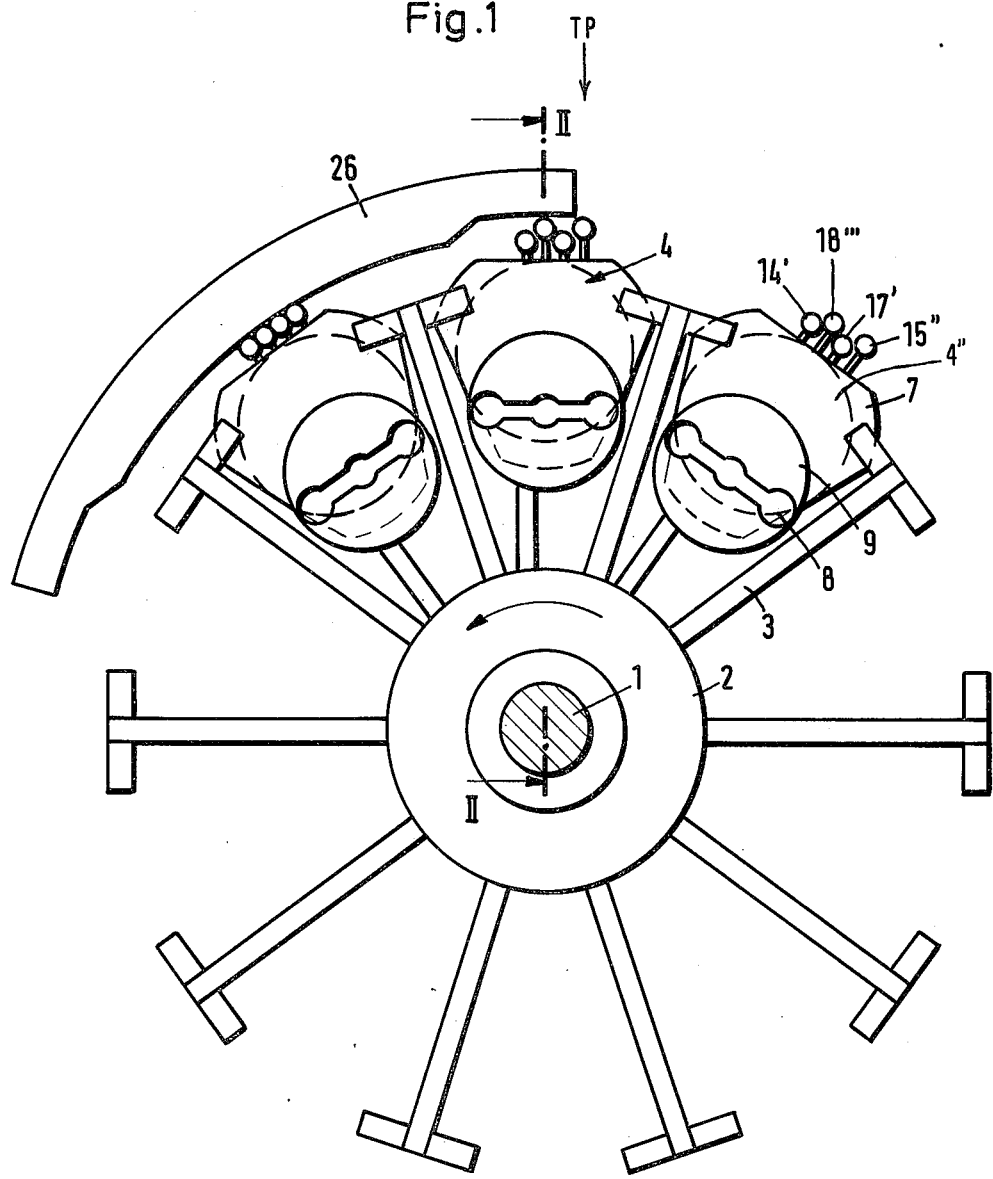
FIG. 1 is an end view of the apparatus according to this invention.

DESCRIPTION OF THE PREFERRED EMBODIMENT:

The apparatus according to this invention has a hub or carousel 2 carried on a horizontal shaft 1 having an axis A and rotatable by means of a motor 40. The carousel 2 has ten radially extending and angularly equispaced identical arms 3 between which are secured by means of readily releasable bolt connections 5 ten identical treatment stations or units 4. Three bolts 5 are provided for securing each of the treatment units 4 to the carousel 2.

Each of the units 4 basically comprises a tamponblank former 6, a press 7, an end rounder 8, and a heating head 9. The press 7 lies axially between the head 9 and the blank former 6.

The heating head 9 is formed with twelve cylindrical holes $9''$ all of whose axes lie on a cylinder $9'$ centered on a rotation axis $9'''$ for the head 9. The gearing 10 serves to rotate this head 9 on the respective unit 4 about the respective axis $9'''$. In addition an arm 11 is engageable in the teeth on the hand 9 to prevent its rotation as will be described below.

Figure 3:
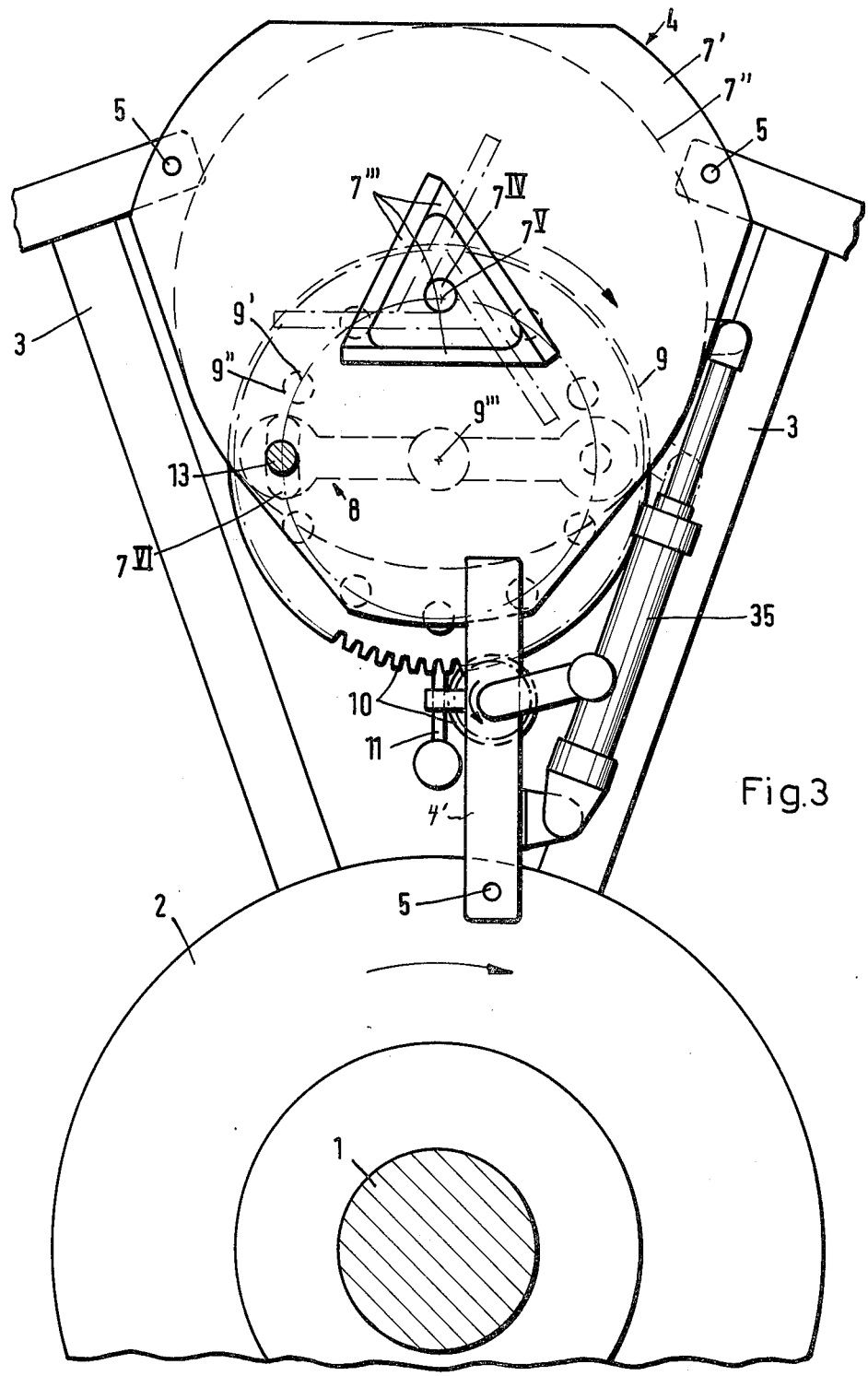
FIGS. 3 and 4 are sections taken along lines III—III and IV—IV of FIG. 2, respectively.

The press 7 is of the general type described in U.S. Pat. No. 2,798,260 whose entire disclosure is herewith incorporated by reference. This press 7 comprises a pair of relatively fixed outer plates or discs $7'$ extending perpendicular to the axes A and $9'''$ and flanking a displaceable inner disc $7''$ connected via cam formations to press elements $7'''$ that are radially displaceable toward and away from an axis $7^V$ so as to form a relatively small opening $7^{IV}$ of cylindrical shape. This hole or recess $7^{IV}$ can be made relatively large and triangular as shown in FIG. 3 in solid lines or relatively small and cylindrical. The axis $7^V$ lies on the circle $9'$ so that the holes $9''$ can be aligned with the hole $7^{IV}$. A pneumatic cylinder 35 is connected at one end to a support arm $4'$ of the support and at its other end to the plate $7''$ so that when pressurized through a valve 36 it can displace this plate $7''$ and displace the elements $7'''$ radially of the axis $7^V$. The rounder 8 has a concave cup-shaped formation $8'$ (FIG. 5F) turned toward the head 9 and is carried on one end of a cylinder 12 itself mounted on one of the plates $7'$ for displacement of this element 8 towad and away from this head 9 parallel to the axis A and the axis $9'''$.

An ejector or pusher rod 13 is axially displaceable through the discs 7' and through an acuate slot 7$^{VI}$ in the disc 7". This pusher rod 13 is aligned with that hole 9" of the heating head 9 which is offset by 270° from the hole aligned with the pressing hole 7$^{IV}$.

Figure 2:
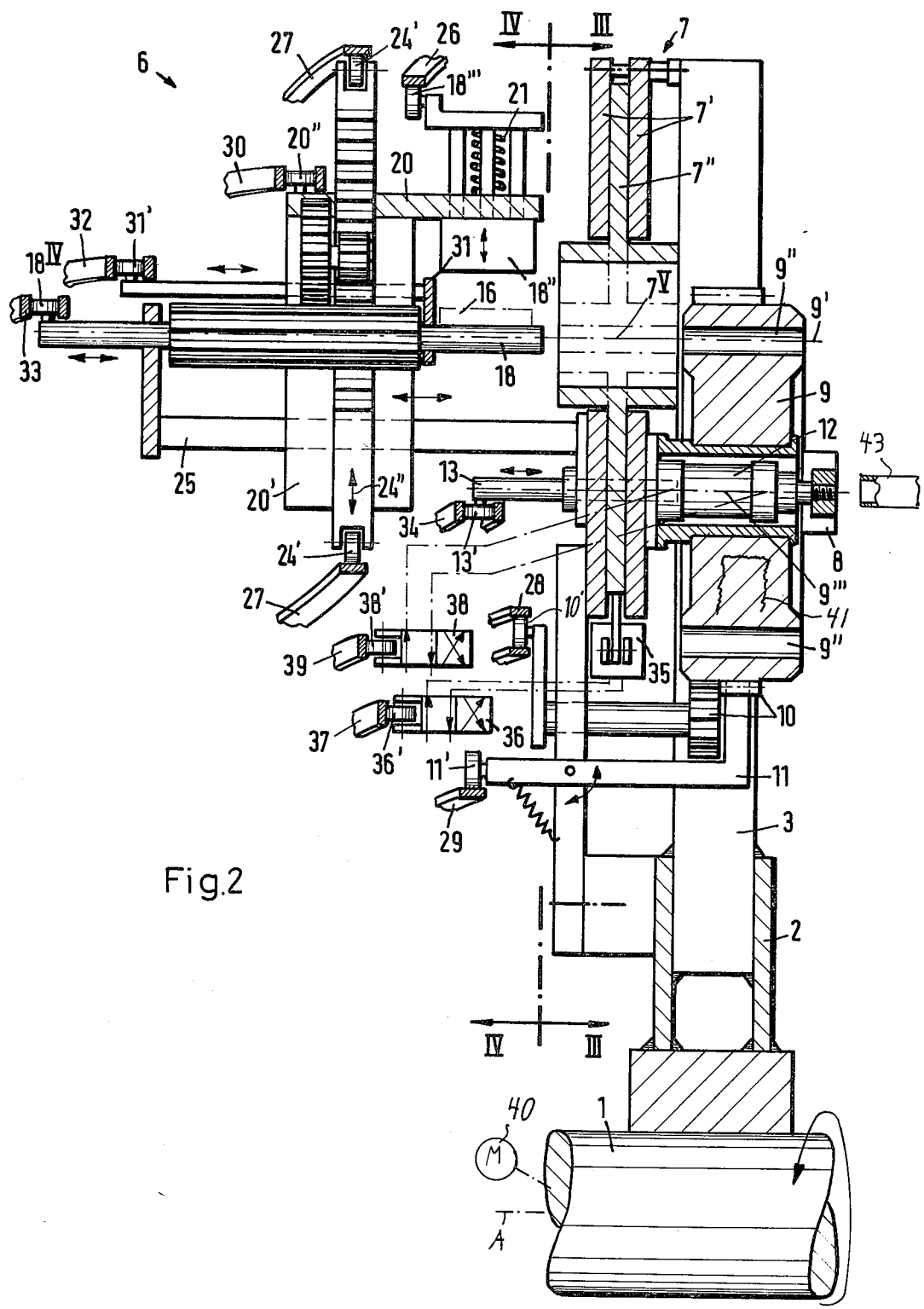
FIG. 2 is a vertical section taken along line II—II of FIG. 1.
Figure 4:
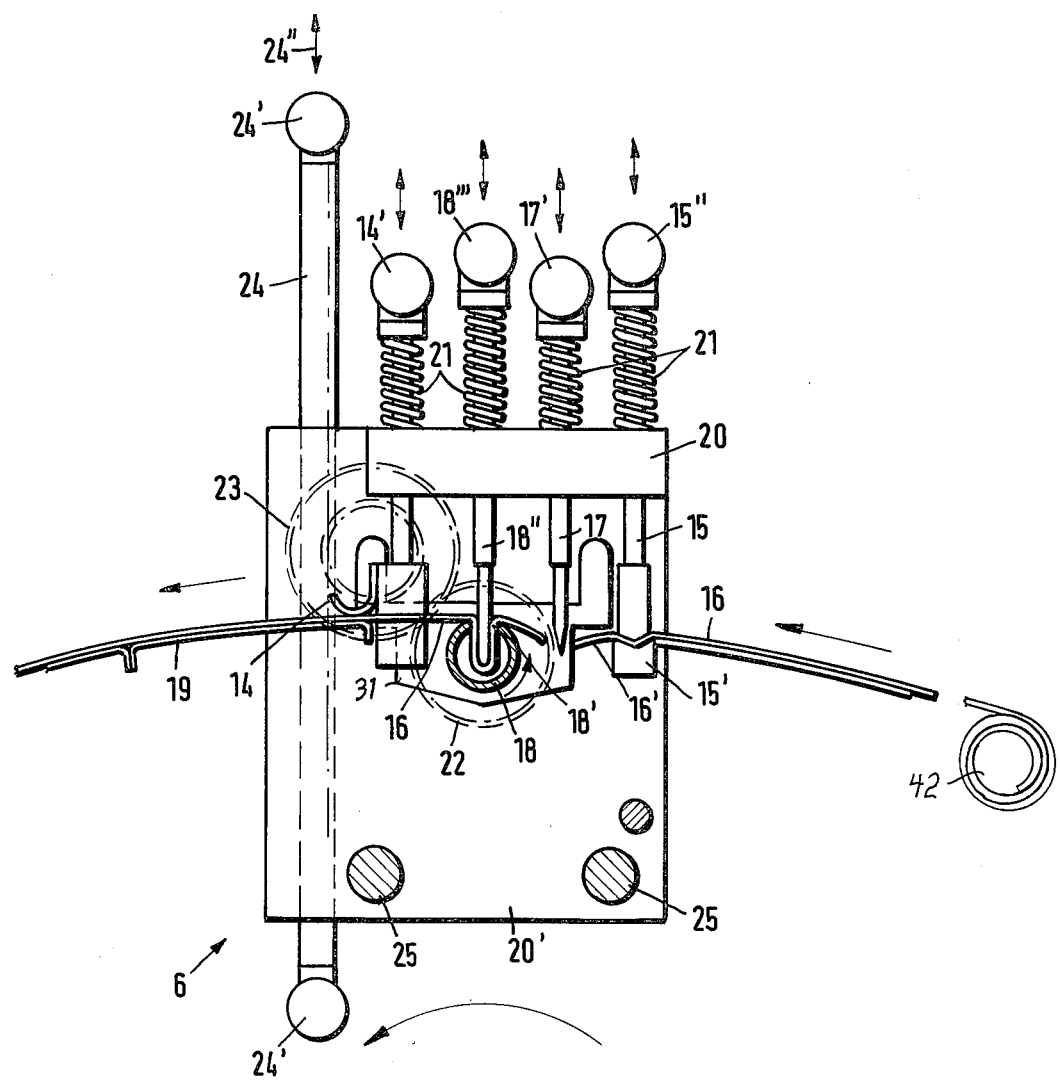

The blank former 6 is best seen in FIGS. 2 and 4 and basically comprises a downstream gripper 14, an upstream gripper 15, a winder 18 between them and a cutter 17 between the winder 18 and upstream gripper 15. The upstream gripper 15 is constituted as a movable element 15 and a fixed anvil element 15' forming a V-shaped slot adapted to grip a strip 16 of strip material and pull it from a supply 42 fixed adjacent the carousel 2. The severing element 17 is a blade reciprocal across the path of the strip 16 between the gripper 15 and the winder 18.

The winder 18 is formed as a mandrel tube 18 having a slot 18' in which is engageable a pusher 18" reciprocal parallel to the blade 17 and holding element 15. This mandrel tube 18 is carried on a gear 22 meshing with the gear 23 itself meshing with a rack 24 provided at its opposite ends with cam-follower rollers 24'. The gripper 14 is formed as a deflectable elastic curved element cooperating with a guide 19 so as to hold the strip 16 snugly against this guide 19 while still allowing it to be pulled between the curved element 14 and the guide 19. The elements 15, 17, 18" and 14 are all displaceable parallel to each other on an upright 20 on a support 20' and all have respective cam-follower rollers 15", 17', 18'" and 14' which cooperate with cams as will be described below. The rack 24 is slidable in the base plate 20' parallel to the other movable elements. These elements are all urged radially outwardly by springs 21. The entire support 20, 20' is displaceable parallel to the axis A on guide rods 25 between a front or advanced position illustrated in solid lines in FIG. 2 and a retracted position to the left of this position.

The support 20' also carries a stripper plate or pusher 31 surrounding the mandrel 18 and displaceable parallel thereto and to the axis A.

The various devices described above are operated by a cam arrangement shown generically in FIG. 1 at 26 which extends around the entire carousel 2. There are two main types of motion, parallel to the axis A and radial to the axis A.

The locking pawl 11 is provided with a cam-follower roller 11' that rides on a cam 29 for radial displacement of this roller 11'. Similarly radially displaceable is the cam-follower roller 10' of the gearing 10, here riding on a radial cam 28. The cam-follower rollers 14', 18'", 17' and 15" all ride on respective non-illustrated radial cams shown generically in FIG. 2 at 26. Similarly another cam 27 is provided for displacement of the rollers 24' radially in the direction of arrow 24".

The pusher or ejector rod 13 has an axial cam-follower roller 13' riding on an axial-displacement cam 34. Similarly the pusher 31 has a cam-follower roller 31' riding on a respective axial-displacement cam 32 and the mandrel 18 has a cam-follower roller 18$^{IV}$ riding on another axial-displacement cam 33. The entire support or housing 20, 20' is axially displaceable by means of a cam 30 engaging a roller 20".

Finally the cylinders 12 and 35 are operated via respective valves 38 and 36 having respective cam-follower rollers 38' and 36' riding on respective axial cams 39 and 37. These last two cams 39 and 37 could also be arranged for radial displacement if desired.

It is noted that the mandrel 18 can move axially between a rear position indicated in solid lines in FIG. 2 and an advanced position in which it lies within the press opening 7$^{IV}$. Similarly the housing 20, 20' and the various elements 15, 17, 18" and 14 thereon are also displaceable between an advanced position indicated in solid lines in FIG. 2 and a withdrawn position to the left of this position. Furthermore the pusher 31 can be advanced from a rearward or withdrawn position shown in solid lines in FIG. 2 to an advanced position immediately adjacent the press 7. All of these motions can take place virtually independently of each other, although it is noted that although the pusher 31 can be advanced before the housing 20, 20', it cannot be withdrawn until this housing 20, 20' and the mandrel 18 are withdrawn.

Figure 5B:
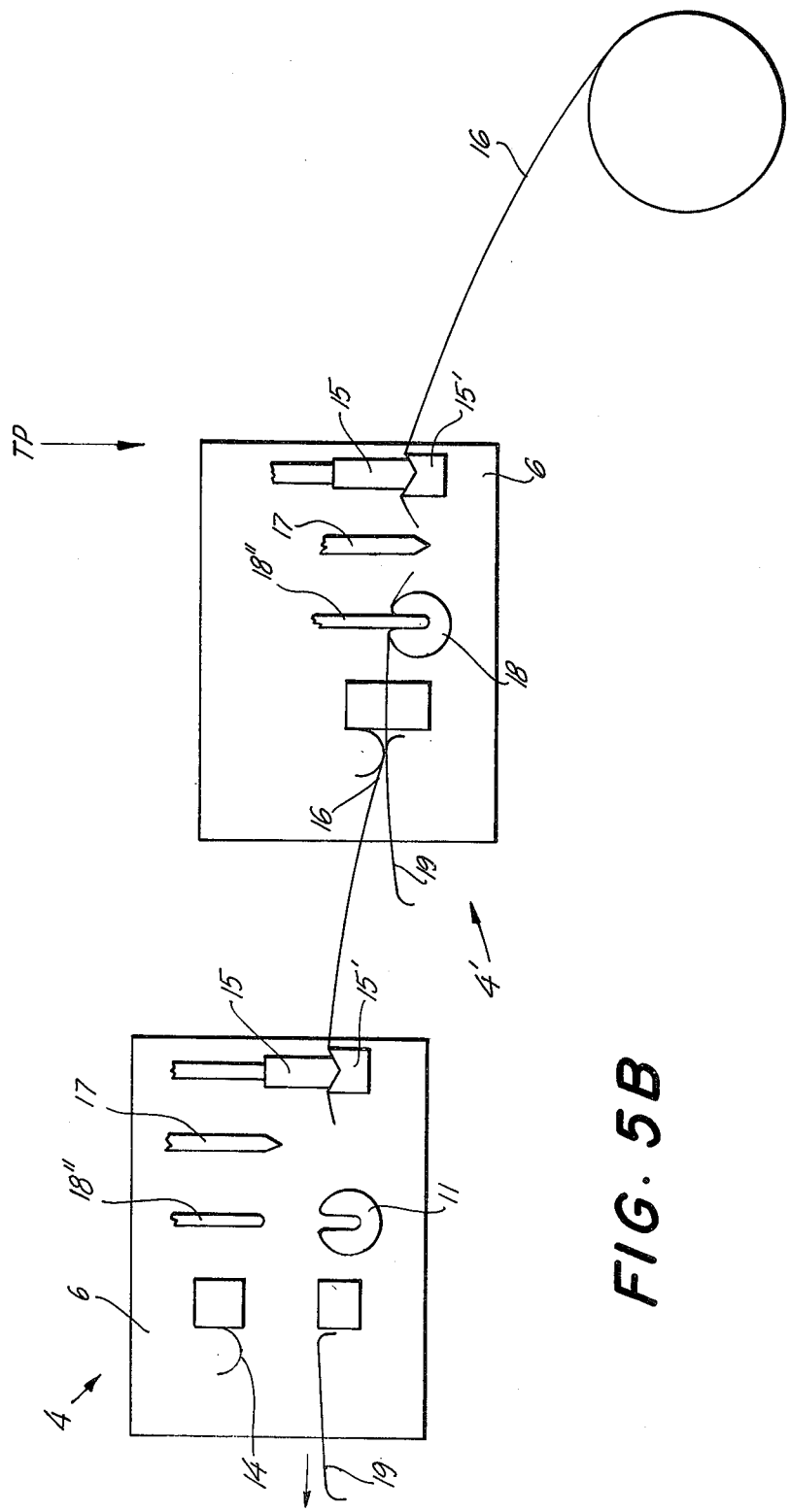

The apparatus described above functions as follows:

As shown in FIG. 5B free end 16' at take-up point indicated by arrow TP of the strip 16 of material to form the tampon is gripped in the upstream grippers 15 of blank former 6 of one of the units 4 which is in the position illustrated in FIG. 2, that is with its mandrel 18 and stripper 31 in the back position and with its housing 20, 20' in the advanced position.

The trailing unit 4', which is approximately 300 mm behind the unit 4 leading it, has its stripper 31 and mandrel 18 in the advanced position, but its housing 20, 20' in the retracted position. This allows the leading unit 4 to pull a section of the strip 16 through the trailing unit 4' without interference by the structure carried on the support 20, 20'. Once the strip 16 is properly positioned on top of the mandrel 18 the cam 30 advances the entire support 20, 20'. The cam 26 then closes down the two grippers 14 and 15 as seen in FIG. 5B and thereafter displaces the blade 17 and pusher 18" into the illustrated dropped positions of FIG. 4. This severs from the strip 16 a portion and forms a new free end 16' on the strip 16, and pushes the trailing end of the cut-off portion into the slot 18' of the mandrel 18.

Figure 5C:
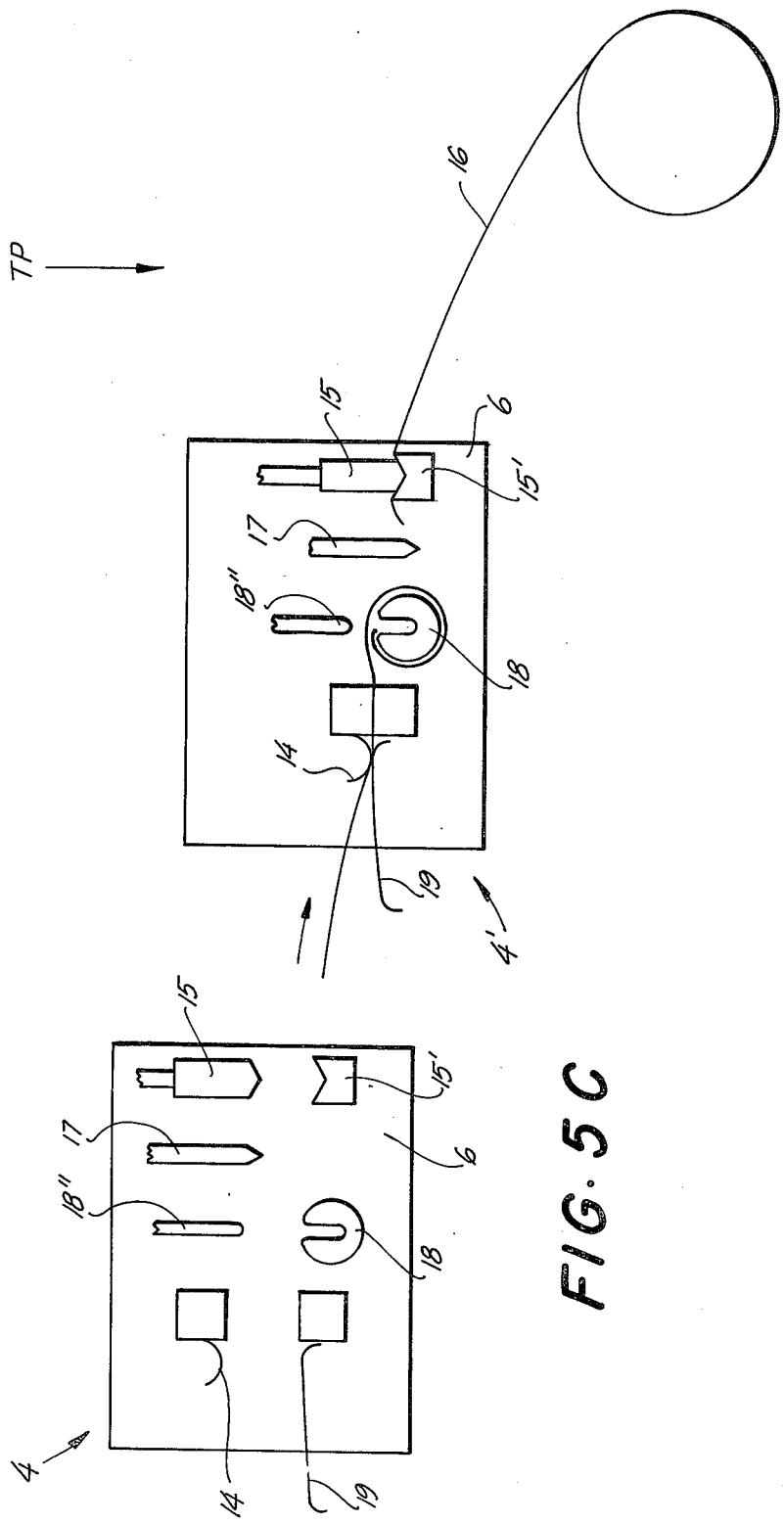

Thereafter as shown in FIG. 5C the leading end of the cut-off strip portion is released from the gripper 15 in the leading unit 4 and the cam 26 allows at least the roller 18'" to rise up under the force of its spring 21 so as to pull the pusher 18" out of the slot 18, whereupon the cam 27 radially displaces the rack 24 in the direction of arrow 24" so as to rotate the mandrel 18 several turns and wind-up the cut-off portion of the strip 16 around itself, thereby forming a tampon blank. It is noted that during this winding-up operation the gripper 14 remains closed with sufficient force to tension the severed portion but without sufficient force to prevent it from being pulled through the gripper 14 and wound up on the mandrel 18.

Subsequently the cams 32 and 33 advance both the stripper 31 and the mandrel 18 so that this mandrel 18 enters into the pressing recess 7$^{IV}$ which is at this time fully opened, and positions the tampon blank therein.

Figure 5D:
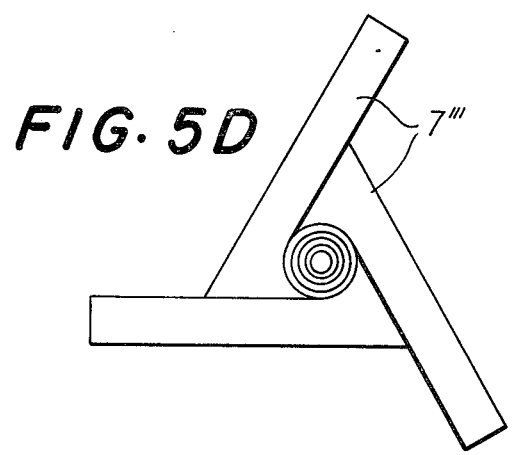

Thereupon the cam 33 withdraws the mandrel 18, while the cam 32 holds the stripper 31 in its advanced position so as to strip the tampon blank off the mandrel 18 and deposit it in the recess 7$^{IV}$. The cam 37 then operates a cylinder 35 by means of the valve 36 so as to radially inwardly displace the pressing elements 7'" and thereby press the tampon blank as shown in FIG. 5D.

After such a pressing the cam 33 again advances the mandrel 18 so that it acts as a pusher to force the pressed tampon out of the hole 7$^{IV}$ and into that hole 9" of the heating head 9 which is aligned on the axis 7$^V$. During such transfer the cam 29 holds the locking pawl 11 in the gearing 10 to prevent any rotational movement of the head 9. As soon as the finished tampon is placed in the heating head 9 the cam 29 withdraws the pawl 11 from the gearing 10 and the cam 28 starts to rotate the head 9 at such a rate that by the time the carousel 2 has made a complete revolution the next hole 9″, which is empty, is aligned with the hole 7^IV. At the same time the cam 37 opens up the press 7 again.

During the next nine revolutions of the carousel 2, during each of which the head 9 is indexed through 30°, the head 9, which is heated to between 100° C. and 135° C. by the resistance wire 41 effectively irons and thermally stabilizes the pressed tampon in the hole 9″.

Figure 5E:
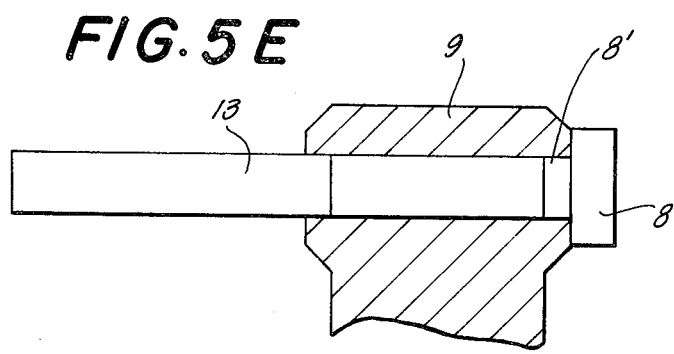
Figure 5F:
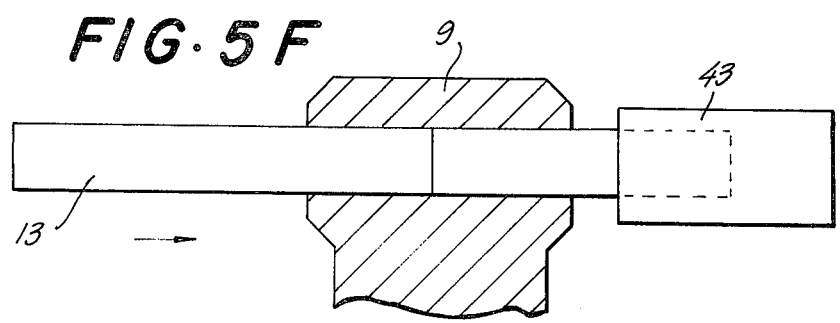

Finally as shown in FIG. 5E when the hole 9″ having the tampon passes through 270° relative to the axis 9‴ it aligns with the pusher 13. The cam 39 at this time operates this valve 38 to pull the rounding element 8 down tight against the thus-heated and pressed tampon and the cam 34 pushes the ejector rod 13 against its opposite end. This rounds the end of the tampon and, once such rounding is completed, the rounding element 8 withdraws. The cam 34 further pushes the rod 13 axially as shown in FIG. 5F so as to eject the finished tampon into an insertion tube such as shown at 43. This operation takes place at the same time as the insertion of a pressed but not heated tampon into the radially outermost hole 9″, that is during an interval in which the pawl 11 is rotationally fixing the head 9.

The machine is normally operated at a rate of nine revolutions per minute, so that the ten units 4 will together produce 90 tampons per minute. An increase in the number of units 4 or in the rotation speed can raise this number and similarly an increase in the number of holes 9″ can increase the heating time which here is approximately 45 seconds. Many modifications or changes of the invention are possible within the scope thereof. For instance the units 4 could be radially displaced 180° on the carousel 2 whereupon the radial cams 26 and 17 and also the axial cams 30, 32 and 33 would have a smaller diameter so as to give the machine a much smaller size. Also it is possible to feed the strip 16 in radially rather than tangentially as shown.

It will be understood that each of the elements described above, or two or more together, may also find a useful application in other types of systems differing from the types described above.

While the invention has been illustrated and described as embodied in a method of and apparatus for making tampons, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of making tampons from a strip of pressable material, said method comprising the steps of:
   (a) continuously orbiting a succession of angularly spaced treatment stations about an axis in a predetermined rotational sense, whereby each of said stations trails on a circular path the station immediately downstream and leads the station immediately upstream;
   (b) continuously withdrawing said strip of pressable material from a supply and feeding said strip in a direction substantially tangential to said circular path, and during each orbit of said stations:
   (c) gripping the end of said strip at a first one of said stations and pulling said strip from said supply as said first station orbits;
   (d) thereafter gripping said strip between said end and said supply at a second station immediately trailing said first station;
   (e) thereafter severing the gripped strip at said second station and releasing the severed strip portion only at said first station, whereby a new end of said strip is formed at said second station;
   (f) thereafter winding said severed portion at said second station up into a tampon blank;
   (g) thereafter pressing said tampon blank at said second station into a finished tampon; and
   (h) thereafter discharging said finished tampon from said second station.

2. The method defined in claim 1, wherein said stations are orbited about said axis at least five times per minute.

3. The method defined in claim 1, wherein said severed portion is wound into a tampon blank in step (g) by wedging the trailing end of said portion in a slotted mandrel at the respective station and thereafter rotating said mandrel.

4. The method defined in claim 3, wherein said finished tampon is discharged in step (h) by pushing same from the station with the respective mandrel.

5. The method defined in claim 1, wherein the gripping of steps (c) and (d) is effected between a pair of holding elements and the severing of step (e) is effected by a blade engageable with said strip, said method further comprising the step (k) of normally urging at least one of each of said pairs of elements and said blade out of engagement with said strip.

6. The method defined in claim 1; further comprising the step (g') of heating said finished tampon in each station in a respective one of a respective array of heating recesses of a heating head in each station, and the step (g″) of angularly indexing each head of each station after each pressing operation to align another of said heating recesses with the respective pressing recess.

7. The method defined in claim 6; further comprising the step (g‴) of angularly arresting the heating head and displacing the finished tampon from the respective pressing recess to a respective heating recess between steps (g) and (g').

8. The method defined in claim 1; further comprising the step (k) of rounding the end of a finished tampon before step (h).

9. A method of making tampons from a continuous strip of pressable material, said method comprising the steps of: continuously orbiting a plurality of angularly spaced treatment stations about an axis; feeding said strip in a direction substantially tangential to to the path of movement of said stations to a take-up point in said path of movement; and, during each orbit of said stations, comprising the steps of gripping in said take-up point a leading portion of said strip at a first station moving past said take-up point; pulling said strip as said first station orbits; gripping in said take-up point a trailing portion of said strip at a second station orbiting past said take-up point; pulling said strip as said second station orbits; severing and holding at said second station the length of the strip defined by the angular displacement of said first station; releasing at said first station said strip and winding the severed strip length at said second station up into a tampon blank; and processing said tampon blank at said second station into a finished tampon, and discharging said finished tampon from said second station before the same returns to said take-up point.

10. The method defined in claim 9, wherein said finished tampons are heated for at least 30 seconds to a temperature of at least 100° C.

11. An apparatus for making tampons from a continuous strip of pressable material, said apparatus comprising: a carousel rotatable about an axis; a plurality of treatment units arranged on said carousel for orbiting on a circular path about said axis; means for feeding said strip, on a path substantially tangential to said circular path, to a take-up point on said circular path; each unit supporting a tampon blank former, and means for processing the formed tampon blank into a finished tampon, each blank former being axially movable to and from said path of feeding and including an upstream gripper for clamping said strip at said take-up point and pulling it till a corresponding gripper in the consequent unit clamps said strip at said take-up point, a severing member for severing a strip portion pulled out by the preceding unit, a winding mandrel for winding up the severed strip portion into a tampon blank and a downstream gripper for tensioning the strip portion during its winding; each tampon blank processing means having at least one inlet passage in alignment with said mandrel and means for transferring the tampon blank from said mandrel into said passage; and actuation means including at least one stationary cam and cam follower means arranged in each unit for activating in a predetermined order said blank former and said processing means.

12. An apparatus as defined in claim 11, wherein each treatment unit is detachably connected to said carousell.

13. An apparatus as defined in claim 12, wherein said carousel has a plurality of radially extending arms between which are provided said units.

14. An apparatus as defined in claim 11, wherein said tampon blank processing means includes a pressing device arranged in operative proximity to said winding mandrel, and means for displacing said tampon blank from said mandrel into said pressing device.

15. An apparatus as defined in claim 14, wherein said actuation means includes a pneumatic cylinder-piston driving member controlled by a valve and arranged for activating said pressing device, said valve being controlled by said stationary cam.

16. An apparatus as defined in claim 11 wherein each blank former includes an axially guided support and said mandrel is supported for axial displacement in said guided support.

17. An apparatus as defined in claim 11; further including a strip holder for holding said strip on said mandrel.

18. An apparatus as defined in claim 17, wherein each gripper, each severing member and each strip holder includes a fixed element and a movable element displaceable toward and away from said fixed element.

19. The apparatus defined in claim 11, wherein said processing means further includes heating means each including a rotatable heating head having a plurality of spaced-apart recesses each shaped to receive a finished tampon, and means for heating said head.

20. The apparatus defined in claim 19, wherein said head of each unit is rotatable in the respective unit about a respective head axis parallel to said carousel axis.

21. The apparatus defined in claim 19, wherein each of said heads has at least twelve such recesses and said carousel is provided with at least ten such units.

22. The apparatus defined in claim 3, wherein said processing means further includes means for rounding an end of a finished tampon.

23. The apparatus defined in claim 11; further comprising adjacent said carousel means for receiving a finished tampon and inserting same into a packing.

* * * * *